United States Patent [19]
Fujita et al.

[11] Patent Number: 4,943,298
[45] Date of Patent: Jul. 24, 1990

[54] CEREBRAL ANEURYSM CLIP

[75] Inventors: Shigekiyo Fujita, 8-22, kitashinzaike 1-Chome, Himeji, Hyogo; Toyokazu Kurushima, Aichi; Hiroaki Kuno, Aichi; Hiromitsu Hiraiwa, Aichi, all of Japan

[73] Assignees: Inax Corporation, Tokoname; Shigekiyo Fujita, Himeji, both of Japan

[21] Appl. No.: 360,588

[22] Filed: Jun. 2, 1989

[30] Foreign Application Priority Data

Jun. 9, 1988 [JP] Japan .................................. 63-142634

[51] Int. Cl.⁵ .............................................. A61B 17/00
[52] U.S. Cl. ..................................... 606/158; 606/151; 606/157
[58] Field of Search ................... 128/334 R, 335, 325, 128/346; 606/151, 157, 158

[56] References Cited

U.S. PATENT DOCUMENTS

| 4,416,266 | 11/1983 | Baucom | 606/158 |
| 4,671,281 | 6/1987 | Beroff et al. | 606/157 |
| 4,706,668 | 11/1987 | Backer | 606/158 |
| 4,765,335 | 8/1988 | Schmidt et al. | 606/158 |
| 4,777,950 | 10/1988 | Kees, Jr. | 606/158 |
| 4,834,096 | 5/1989 | Oh et al. | 606/158 |

FOREIGN PATENT DOCUMENTS

| 3302707 | 12/1983 | Fed. Rep. of Germany . | |
| 2555952 | 6/1985 | France . | |
| 54-7788 | 1/1979 | Japan | 606/158 |
| 59-8948 | 1/1984 | Japan | 606/158 |
| 61-205517 | 12/1986 | Japan | 606/158 |

OTHER PUBLICATIONS

Engineering in Medicine, vol. 6, No. 4, Oct. 1977, pp. 123–124.
Medical & Biological Engineering & Como., vol. 18, No. 4, Jul. 1980, pp. 503–509.

Primary Examiner—Randall L. Green
Assistant Examiner—Gary Jackson
Attorney, Agent, or Firm—Kanesaka and Takeuchi

[57] ABSTRACT

A cerebral aneurysm clip composed of blade parts capable of clipping the root of a lump of cerebral aneurysm and a spring part of imparting a clipping force to the said blade parts, which is characterized in that the said blade parts are made of a synthetic resin or ceramic.

9 Claims, 4 Drawing Sheets

CEREBRAL ANEURYSM CLIP

FIELD OF THE INVENTION AND RELATED ART STATEMENT

The present invention relates to a cerebral aneyrysm clip and, in particular, to that which may apply to a patient with no trouble in X-ray CT (computed tomography) or NMR (nuclear magnetic resonance)-CT examination.

Cerebral aneurysm is caused by expansion of the artery of a brain in the form of a lump, and when it is broken, it would cause subarachnoid hemorrhage or the like serious condition to endanger the life.

Prior to the surgical operation on the cerebral aneurysm, the existence thereof is first ascertained by X-ray CT or NMR-CT as cerebral angiography, and thereafter the root part of the lump is clipped with a particular metal clip which is called a cerebral aneurysm clip whereby the surgical operation is finished. After the operation, the clip used is kept in the brain as it is.

Hitherto, various proposals have been made on the shape and the material of the cerebral aneurysm clip, but the clips which have heretofore been proposed and actually used for the purpose are metallic or are made of a stainless steel or a Co-Cr alloy (Japanese Patent Application Laid-Open Nos. 54-4488 and 59-8948, and Japanese Utility Model Application Laid-Open No. 61-205517).

However, where the body to be examined by X-ray CT has a metal or the like substance therein during the examination, X-ray would be reflected and scattered on the surface of the substance to give an artifact on the image photographed and, as a result, the result of the examination could not be accurately read out from the image. As NMR-CT uses a strong magnetic field (recently about 2 tesla or so) and a high frequency, existence of a magnetic substance in the body to be examined would cause a noticeable strain in the image obtained or the clip (magnetic substance) would be moved or heated in the body (brain) during examination by NMR-CT. In addition, existence of an electroconductive metal in the body would also be dangerous, since the metal would generate an induced current in a magnetic field or high frequency field and the current would damage the body. Furthermore, other many problems on the metal clip for clinical NMR-CT examination have variously been reported and investigated in the field. For instance, it is reported in NMR Medical Technology, Vol. 4, No. 2 (1984), pages 20 to 23 with title of "Influence of Static Magnetic Field to Metal in Body", that NMR-CT should not be effected on the patent having a metal clip in the body.

Under the situation, there is an extremely serious problem that the patent who had an operation on its cerebral aneurysm and therefore have a metal clip in its brain could no more undergo an X-ray CT or NMR-CT examination, which has an important role in the cerabral surgical operation such as operation on cerebral aneurysm, after the operation.

OBJECTS AND SUMMARY OF THE INVENTION

One object of the present invention is to overcome the above-mentioned problems in the prior art and to provide a cerebral aneurysm clip which does not give a troule to CT-examination after the operation with the clip.

Another object of the present invention is to provide a cerebral aneurysm clip which is chemically stable and harmless to a living body and which has excellent corrosion-resistance, durability and mechanical characteristics.

In accordance with the present invention, there is provided a cerebral aneurysm clip composed of blades to clip the root of a cerebral aneurysm and a spring to impart a clipping force to the said blades, which is characterized in that the blades are made of a synthetic resin.

In accordance with the present invention, there is further provided a cerebral aneurysm clip composed of brades to clip the root of a cerebral aneurysm and a spring to impart a clipping force to the said blades which is characterized in that the blades are made of a ceramic.

DESCRIPTION OF THE PREFERRED EMBODIMENTS

Figure 1:
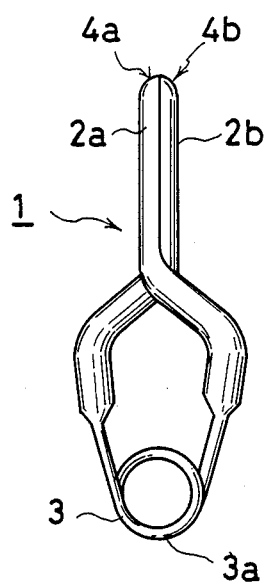
FIG. 1 is a front view to show one embodiment of the cerebral aneurysm clip of the present invention.

In the first invention, the synthetic resin for forming the blades is one which satisfies the requirements that it does not decomposed or, for example, does not hydrolyzed with a body juice (physiological salt solution), it does not release a substance having a harmful influence on a body, and it does not absorb water. For instance, fluorine resins, methacrylic resins and other thermoplastic resins such as polyethylene, polypropylene or polystyrene can be used. In addition, the blades may also be made of thermosetting resins such as epoxy resins, silicon resins or unsaturated polyester resins. Preferred examples of the resins include, for example, polymethyl methacrylate, polytetrafluoroethylene, silicon resins and polyether sulfone. Further, the blades may also be made of a material comprising the above-mentioned resin and a reinforcing agent, for example, a fiber-reinforced synthetic resin. As the reinforcing fibers for constituting the fiber-reinforced synthetic resin, there are preferably mentioned carbon fibers such as graphite whiskers, alumina fibers such as alumina whiskers, SiC fibers such as SiC whiskers, glass fibers (especially preferably those having a low content of heavy metal oxides or phosphates) and high polymer fibers.

In the first invention, as the material of forming the spring are preferably used the same plastics as those for the above-mentioned blades. In this case, as the whole of the cerebral aneurysm clip is made of a synthetic resin, the blades and the spring can easily be made of the same synthetic resin so that a whole and the manufacture cost is low. In particular, the formation of the spring is easy, and the spring may have the spring function because of the elasticity of the synthetic resin whereby a strong clipping force can be imparted to the blades. In addition, as synthetic resins are easily worked or machined, the synthetic resin clip can be cut or shaved into a proper shape in operation so that the shape of the clip may properly be conformed to the affected part of the patient. Moreover, as synthetic resins are chemically stable and are durable and those which are harmless to a living body can be selected for use, the condition of the operated part in the patent can be maintained well. Further, as synthetic resins do not have any bad influence on X-ray CT or NMR-CT examination, there is no trouble on the X-ray CT or NMR-CT examination on the patient operated. When a patient undergoes an operation for cerebral aneurysm with the clip of the present invention as mentioned above and then undergoes an X-ray CT or NMR-CT examination, the image photographed has no artifact and therefore has no strain as the clip used is one made of a synthetic resin. In addition, any induced current is not generated during the examination. Accordingly, after the operation with the clip of the present invention, the patient can undergo an X-ray CT or NMR-CT examination with no danger on the body of itself.

As one preferred embodiment of the first invention, the spring may be made of a fiber-reinforced synthetic resin, whereby the spring force may be reinforced.

In the second invention, the blades are made of a ceramic, which is preferably one having an HN value in X-ray CT of 2500 or less.

The HN value in X-ray CT indicates the value of an attenuation constant of each material. Specifically, it indicates a factor to represent the transmittance of X-ray, where water is defined to have the value of 0, air to have the value of −1000 and bone to have the value of 1000. (In this connection, an image is formed in CT because of the excellent resolving power (density resolving power or attenuation constant resolving power) to the attenuation constant.)

Precisely, CT value is generally represented by the following formula:

$$CT\ \text{Value} = \frac{\mu_t - \mu_w}{\mu_w} \times K$$

where $\mu_t$ means the attenuation constant of the material; $\mu_w$ means the absorption constant of water; and $K$ means a constant.

Where $K=1000$, the value is an HN value in X-ray CT. Preferably, ceramics having an HN value in X-ray CT of 2000 or less, which are insulating materials at room temperature and have a high strength and which are free from the problem of artifact in a high magnetic field or high frequency field, are used in the present invention.

Various ceramics are shown in Table 1 below, together with the HN vlaue in X-ray CT and the degree of artifact.

TABLE 1

| Material | HN Value in X-ray CT | Artifact |
| --- | --- | --- |
| Inconel (Sugita Clip was measured.) | 7000 | Extremely Strong |
| Alumina | 2000 | Somewhat |
| Bone China | 1000 | Only Little |

TABLE 1-continued

| Material | HN Value in X-ray CT | Artifact |
| --- | --- | --- |
| Zirconia | 9000 | Extremely Strong |
| Apatite Ceramic | 3600 | Fairly Noticeable |
| Carbon Fiber-Reinforced Apatite | 3900 | Fairly Noticeable |
| Apatite Glass | 5300 | Fairly Strong |
| AlN | 1100 to 1500 | Somewhat |
| Sialon | 2400 | |
| Silicon Nitride | 1800 to 2300 | Only a Little |
| Silicon Carbide | 6300 to 9300 | No |

As is obvious from Table 1 above, alumina, bone chine, AlN, sialon, silicon nitride and silicon carbide are preferred for use in the present invention in view of the HN value in X-ray CT and of the artifact, but bone chine is unsuitable to the present invention as it has a poor strength. From the viewpoint of the electric insulating property, alumina, AlN and silicon nitride are preferred for use in the present invention.

A cerebral aneurysm clip is required to have a high clipping power capable of strongly clipping the cerebral aneurysm, but it is extremely difficult to expect ceramics to have such spring function.

In accordance with the present invention, therefore, a material which is harmless to living bodies and are hardly deteriorated and which does not have any bad influence on X-ray CT or NMR-CT but has a high spring function is used for forming the spring part of the clip of the invention. As such material for the spring part is preferred rubber such as silicone rubber or the above-mentioned FRP (fiber-reinforced plastic). In particular, FRP is effective from the viewpoint of the strength, corrosion-resistance and durability.

Accordingly, the cerebral aneurysm clip of the first invention may easily be manufactured by first forming the blades from a sintered substance of a determined ceramic or a CVD-coated substance thereof and then joining them to a spring part as separately formed from, for example, FRP.

In accordance with the second invention, the blades are made of a ceramic and the spring is made of a synthetic resin such as a fiber-reinforced synthetic resin, whereby a clip which can safely be used in a living body because of the excellent chemical stability, corrosion-resistance, durability as sell as mechanical characteristics such as high strength of the ceramic can be obtained. In addition, the clip may have a satisfactory clipping force in the blades because of the elasticity of the synthetic resin. Further, the synthetic resin does not have any bad influence on a living body and additionally the ceramic and synthetic resin are non-magnetic materials and therefore do not have any bad influence on X-ray CT or NMR-CT examination. Accordingly, after the clip of the kind of the invention is used in an operation forcerebral aneurysm, the patient thus operated may generally undergo the successive X-ray CT or NMR-CT examination. In particular, where a ceramic having a relatively high X-ray transmittance, for example, an HN value in X-ray CT of 2500 or less, is used for forming the clip of the invention, the clip does not interfere with the image in X-ray CT so that the image in X-ray CT may noticeably be improved.

Now, some embodiments of the present invention will be explained hereunder with reference to the drawings attached hereto.

The embodiments to be explained hereunder with reference to the drawings are mere examples to illustrate the present invention but not to intended to restrict the scope of the present invention. Use of the clips of the present invention can appropriately be effected by one skilled in the art in accordance with the shape and size of the lump of cerebral aneurysm to be treated.

Figure 2:
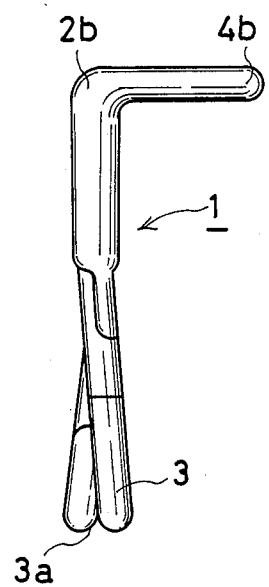
FIG. 2 is a side view to show the same.

FIG. 1 and FIG. 2 show one embodiment of the cerebral aneurysm of the first invention. In the embodiment, clip (1) is composed of a pair of blade parts (2a) and (2b) which are positioned to face to each other and spring part (3) in the form of a ring which is integrated with stems of the blade parts (2a) and (2b). The top of each of the blade parts (2a) and (2b) is bent at an angle of 90° to form the clipping parts (4a) and (4b), respectively, whereby clipping of a lump of cerebral aneurysm may be effected by the use of the clip of such constitution with ease. The blade parts (2a) and (2b) may be opened and shut on the basis of the base end (3a) of the spring part (3) as the fulcrum. As the spring part (3) is formed in the form of a ring, it gives a clipping force to the blade parts (2a) and (2b) because of the elasticity of itself.

In the clip (1) of this embodiment, all the said blade parts (2a) and (2b) and spring part (3) are made of a synthetic resin.

Figure 3:
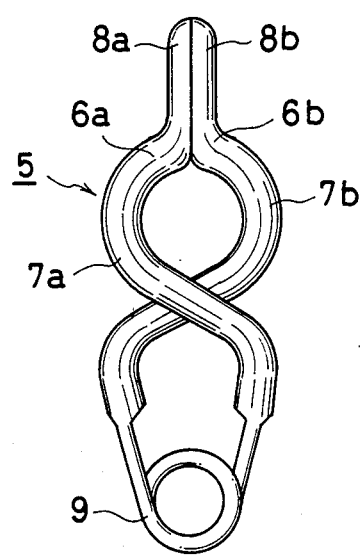
FIG. 3 is a front view to show another embodiment of the cerebral aneurysm clip of the present invention.
Figure 4:
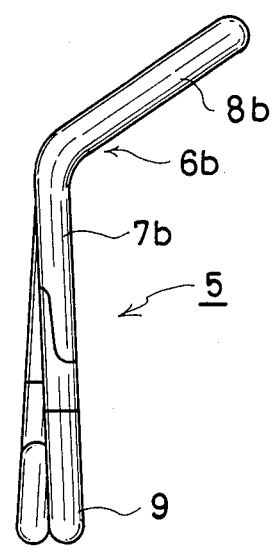
FIG. 4 is a side view to show the same.

In the cerebral aneurysm clip (5) shown in FIG. 3 and FIG. 4, the blade parts (6a) and (6b) are composed of the outwardly curved curve parts (7a) and (7b) and the clipping tops (8a) and (8b), respectively, where the parent artery vessel is put between the curved parts (7a) and (7b) and the root of the lump is strongly clipped between the clipping parts (8a) and (8b) because of the clipping force of the spring part (9).

Figure 5:
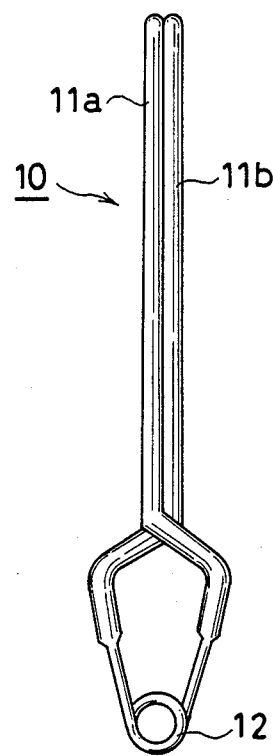
FIG. 5 is a front view to show still another embodiment of the cerebral aneurysm of the present invention.

The clip (10) shown in FIG. 5 has a pair of prolonged blade parts (11a) and (11b), where the opening and shutting dimension in the top ends of the blade parts are enlarged. This may apply to a large size lump of cerebral aneurysm. Such prolonged constitution is so intended that the blade parts may properly be cut in operation so as to vary the length of the blades.

In the clips (5) and (10) shown in FIG. 3, FIG. 4 and FIG. 5, the constitution of the spring parts (9) and (12) is the same as that shown in FIG. 1 and FIG. 2. The clips (5) and (10) shown in FIG. 3, FIG. 4 and FIG. 5 are wholly made of a synthetic resin, like the clip (1) shown in FIG. 1 and FIG. 2.

FIG. 6 to FIG. 10 show embodiments of the cerebral aneurysm clip of the second invention.

Figure 6:
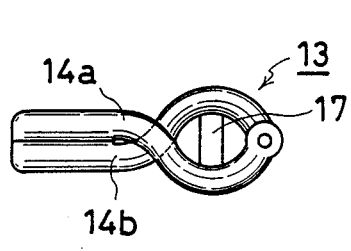
FIG. 6 to FIG. 10 are front views, each of which shows a different embodiment of the present invention.
Figure 11:
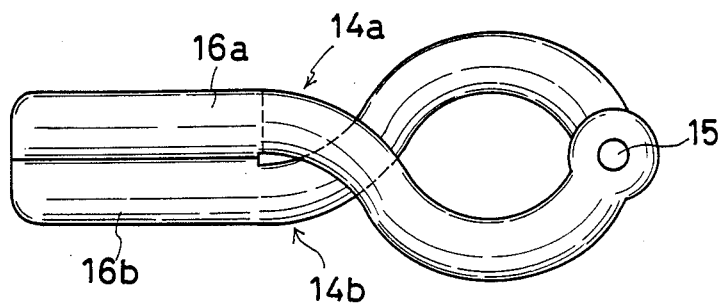
FIG. 11 is a front view to show the blades used in the clips of FIG. 6 and FIG. 7.
Figure 12:
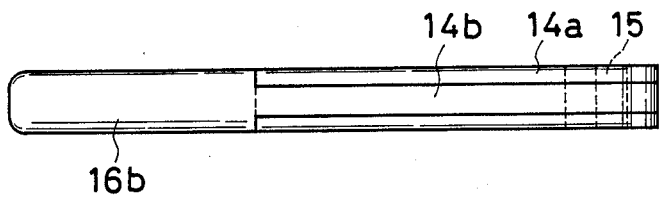
FIG. 12 is a side view to show the same.

In the clip (13) shown in FIG. 6, a pair of blade parts (14a) and (14b) as positioned to face to each other are made of a ceramic. The pair of blade parts (14a) and (14b) have a function of clipping a lump of cerebral aneurysm between the clipping parts (16a) and (16b) on the basis of the joint part (15) as the fulcrum, as shown in FIG. 11 and FIG. 12. In this embodiment, a hopping type spring part (17), for example a spring rod made of a synthetic resin, is inserted into the gap formed between the blade parts (14a) and (14b) composed of the joint part (15) and the clipping parts (16a) and (16b), whereby the clipping power is imparted to the blade parts by the action of the spring part.

In such constitution, the spring part (17) is compressed when the clipping parts (16a) and (16b) of the blade parts (14a) and (14b) are to be opened, while a strong clipping force may be obtained by the function of the spring part (17) when the clipping parts (16a) and (16b) clip a lump of cerebral aneurysm.

Figure 7:
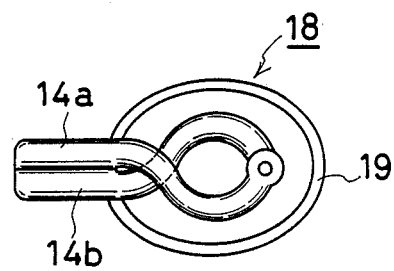

The clip (18) shown in FIG. 7 is composed of blade parts (14a) and (14b) of FIG. 11 and FIG. 12 and a ring-shaped scissor type synthetic resin spring part (19) as integrated therewith. In the constitution, the ring-shaped spring part (19) has a function of imparting a clipping force to the clipping parts (16a) and (16b) which are in the top of the blade parts (14a) and (14b), respectively.

Figure 8:
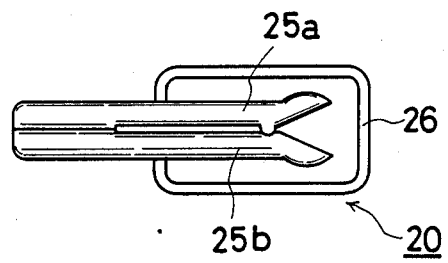
Figure 9:
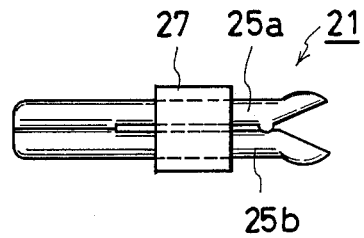
Figure 10:
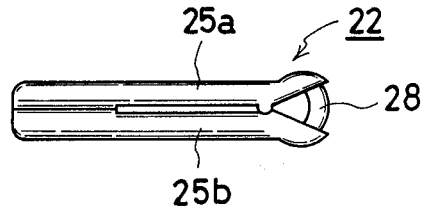
Figure 13:
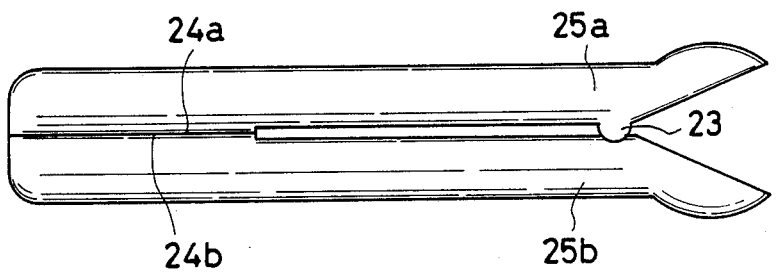
FIG. 13 is a front view to show the blades used in the clips of FIG. 8 to FIG. 10.
Figure 14:
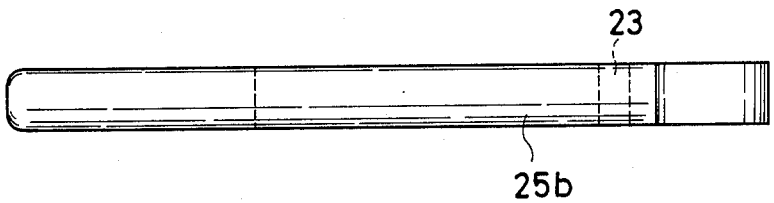
FIG. 14 is a side view to show the same.

The clips (20), (21) and (22) shown in FIG. 8 to FIG. 10, respectively, are composed of blade parts (25a) and (25b) of FIG. 13 and FIG. 14, where the clipping parts (24a) and (24b) are constituted to clip a lump of cerebral aneurysm therebetween on the basis of the joint part (23) as the fulcrum, and a different spring part. Specifically, the clip (20) of FIG. 8 has a squared ring-shaped spring part (26) made of a synthetic resin; and the clip (21) of FIG. 9 has a sheath-type spring (27) made of a synthetic resin, with which the blade parts are sheathed. In the constitution of the clips (20) and (21), when the blade parts (25a) and (25b) are opened, a clipping force is imparted to the clipping parts (24a) and (24b) because of the elastic force of the spring parts (26) and (27).

In the clip (22) of FIG. 10, a plastic spring part (28) is sandwiched between the opened ends of the blade parts (25a) and (25b) in the side of the fulcrum (23). Also in the constitution of the clip (22), when the clipping parts (24a) and (24b) of the blade parts (25a) and (26b) are opened, the spring part (28) is compressed whereby a clipping force is imparted to the clipping parts (24a) and (24b) of the blade parts (25a) and (25b).

As mentioned in detail in the above, the cerebral aneurysm clip of the present invention does not have any bad influence on an X-ray CT or NMR-CT examination. Accordingly, where the clip of the present invention is used in an operation for a cerebral aneurysm, the patient thus operated can undergo the following X-ray CT or NMR-CT examination. It is therefore admitted that the present invention noticeably contributes to the progress of clinical medicine.

In addition, the clip of the present invention is chemically stable and is harmless to living bodies and additionally it has excellent corrosion-resistance, durability and mechanical characteristics. Accordingly, the operated part may favorably be kept good when the clip of the invention is used in the operation.

What is claimed is:

1. A clip for cerebral aneurysm comprising a means which is made of a ceramic and which has a function of clipping a root part of a lump of cerebral aneurysm and a spring means which has a function of imparting a power for clipping said root part to said clipping means.

2. The clip for cerebral aneurysm as claimed in claim 1, in which the clipping means is made of a ceramic having an HN value in X-ray CT of 2500 or less.

3. The clip for cerebral aneurysm as claimed in claim 2, in which the ceramic is selected from the group consisting of alumina, AlN, sialon, silicon nitride and silicon carbide.

4. The clip for cerebral aneurysm as claimed in claim 3, in which the ceramic is alumina, AlN or silicon nitirde.

5. The clip for cerebral aneurysm as claimed in claim 2, in which the clipping means is made of a ceramic having an HN value in X-ray CT of 2000 or less.

6. The clip for cerebral aneurysm as claimed in claim 1, in which the spring means is made of a rubber or synthetic resin.

7. The clip for cerebral aneurysm as claimed in claim 6, in which the synthetic resin is selected from the group consisting of polyethylenes, polypropylenes, polystyrenes, methacrylic resins, epoxy resins, silicone resins, unsaturated polyester resins and fluorien resins.

8. The clip for cerebral aneurysm as claimed in claim 7, in which the synthetic resin is polymethyl methacrylate, polytetrafluoroethylene, silicone resin or polyether sulfone.

9. The clip for cerebral aneurysm as claimed in claim 8, in which the fiber is carbon fiber, alumina fiber, SiC fiber, glass fiber or high polymer fiber.

* * * * *